United States Patent

Camplin et al.

[19]

[11] Patent Number: 5,866,820
[45] Date of Patent: *Feb. 2, 1999

[54] COIL VOLUMETRIC AND SURFACE DEFECT DETECTION SYSTEM

[76] Inventors: Kenneth R. Camplin, 102 Goose Meadow Dr., Forest, Va. 24551; Dennis D. Lang, 2000 Oak Park Pl., Lynchburg, Va. 24503; Darrel P. Kohlhorst, 129 Perry La., Goode, Va. 24556; Daniel P. Geier, 2305 Gravesmill Rd., Forest, Va. 24551; Gary D. Novak, Rt. 2 Box 1029, Altavista, Va. 24517; Sean M. Fitzpatrick, 103 Glenn Haven Terrace, Goode, Va. 24556; Glenn E. McNeelege, 143 Sailview Dr., Forest, Va. 24551; Bradley E. Cox, 241 Whitestone Dr., Lynchburg, Va. 24502; Richard C. Brewer, Rte. 3, Box 267A5, Lynchburg, Va. 24504; Thomas A. Artman, Rt. 1 Box 483B-1, Moneta, Va. 24121; Mark A. Hooker, Rt. 7, Box 62KM, Lynchburg, Va. 24503

[ * ] Notice: This patent issued on a continued prosecution application filed under 37 CFR 1.53(d), and is subject to the twenty year patent term provisions of 35 U.S.C. 154(a)(2).

[21] Appl. No.: 718,257

[22] Filed: Sep. 20, 1996

[51] Int. Cl.⁶ .......................... G01N 29/10; G01N 29/26
[52] U.S. Cl. .................. 073/643; 73/159; 73/597; 73/598; 73/602
[58] Field of Search ....................... 73/643, 159, 620, 73/622, 597, 598, 602; 364/508

[56] References Cited

U.S. PATENT DOCUMENTS

| | | | |
|---|---|---|---|
| 3,850,028 | 11/1974 | Thompson et al. | 73/643 |
| 4,100,809 | 7/1978 | Bobrov et al. | 73/643 |
| 4,104,922 | 8/1978 | Alers et al. | 73/643 |
| 4,307,616 | 12/1981 | Vasile | 73/643 |
| 4,372,163 | 2/1983 | Tittmann et al. | 73/597 |
| 4,466,287 | 8/1984 | Repplinger et al. | 73/643 |
| 4,495,587 | 1/1985 | Plante et al. | 73/602 |
| 5,085,082 | 2/1992 | Cantor et al. | 73/643 |
| 5,237,874 | 8/1993 | Latimer et al. | 73/643 |
| 5,439,157 | 8/1995 | Geier et al. | 228/9 |
| 5,474,225 | 12/1995 | Geier et al. | 228/102 |
| 5,537,876 | 7/1996 | Davidson et al. | 73/624 |

OTHER PUBLICATIONS

Disclosure of Physical Machine and Product Information at AISE Convention, Pittsburgh, PA. Sep. 25, 1995.

Primary Examiner—Hezron Williams
Assistant Examiner—Rose M. Miller
Attorney, Agent, or Firm—Daniel S. Kalka; Robert J. Edwards

[57] ABSTRACT

A EMAT inspection system is utiliized on sheet metal prior to it being formed or rolled to identify surface defects and sub-surface defects such as pencil pipe inclusions by using ultrasonic Lamb waves with the results being displayed on a remote screen of a display and control system which also records the inspection results and controls the EMAT system.

10 Claims, 2 Drawing Sheets

COIL VOLUMETRIC AND SURFACE DEFECT DETECTION SYSTEM

BACKGROUND OF THE INVENTION

1. Field of the Invention

The present invention relates in general to an automated system for non-destructive inspection of metal through the use of EMAT (electromagnetic acoustic transducer) technology and more specifically to the use of such systems to detect surface and sub-surface pencil pipe defects in sheet metal.

2. Description of the Related Art

A variety of industries use sheet metal which is produced typically at a factory from ingots processed by a rolling mill. Ingots are heated and rolled by the mill into a long flat sheet which is then wound into a coil at the end of the mill. Thereafter, the coil is removed from the mill and shipped to other sections of the factory where further treatment processes are performed. To make these other processes have fewer interruptions, the coil maybe unrolled and joined at one of its ends to the end of another coil by welding apparatus. Any number of coils may be welded together in such fashion, depending on the desired length of process run.

Internal inclusions such as non-metallic inclusions and surface defects that may be found in processed metal rolls cause severe problems in down stream applications. When metal is drawn or formed, inclusions can result in surface blemishes, weak spots or tears in the product. In high quality applications, surface scratches can render the ultimate product useless and rejectable. Considering today's market, it's important to find these facts as soon as possible in order to take corrective action or to reroute the product to a less critical application. The rolled metal line is one possible place to locate these defects and begin volume inspection.

The detection of internal (volumetric) defects in steel rolls or plate using ultrasonics has been widely reported. Ultrasonic inspection methods are capable of detecting extremely small volume flaws in strip steel, but are limited due to the need to maintain couplant between the transducer and the steel strip. At a minimum, this couplant requirement slows the test speeds considerably, can introduce errors into the test results, and, in many cases, prevents the test from being performed at all.

The strip steel industry has a particular manufacturing problem of non-metallic inclusions in their strip steel product for use in the automotive/appliance industry which is manifested after the rolling operation. The "pencil pipe" inclusion is not likely to be visible prior to cold rolling. A method or other forming processes of detecting these, and other, inclusions prior to downstream processes is needed that could be used for on-line detection of pencil pipe defects in strip steel before the strip is rolled or formed to final product.

The pencil pipe inclusions are thought to result from extraneous non-metallic material trapped in the ingot that finally gets rolled into a thin inclusion or delamination. The defect typically occurs close to the edge of the strip (within about 25" of the edge).

In an ultrasonic technique, defects are detected through their interference with ultrasonic waves which are generated and detected by the interaction between a static magnetic field ($B_o$) and eddy currents (g) induced by a high frequency magnetic field ($B_o$).

This interaction allows the converting electromagnetic energy to mechanical energy and gives rise to two basic forces respectively known as:

$F_L$=the LORENTZ force due to the interaction between free electrons and crystal lattice.

$F_M$=the magnetostrictive force due to local magnetization and its related striation.

In the case of ferromagnetic materials (such as carbon steels) $F_M$ is about 10 to 100 times higher than $F_L$.

In case of non-ferromagnetic materials (such as austenitic steels), $F_M$ is not present and $F_L$ only can be used for generation and detection.

Both Lorentz and magnetostrictive forces generate ultrasonic waves which are elastic waves that consist of oscillations of the crystal lattice of the metal around its equilibrium position. These ultrasonic waves are of two types, respectively:

guided waves including plate waves, and bulk waves or free waves.

Plate waves more particularly Lamb waves are preferred because they move as guided waves through the material, which results in a much higher detectivity.

In known detection systems such as a EUROPA system, each pole of the magnet is located under the strip and ultrasonic waves are merely produced across the width direction while the strip is moving.

These Lorentz and magnetostriction effects are reversible. This means that ultrasounds will interact with magnetic field, by producing electromagnetic waves which can be detected by coil-type receivers similar to those used as emitters.

By a suitable design of the transducers and of the magnetic field, Lamb waves are efficiently generated and consist of an optimal combination of longitudinal and transverse waves.

Two types of excitation modes can be used respectively s=symmetrical and a=non-symmetrical. These modes are characterized by the evolution of the virtual reflection factor across the thickness. Surface defects and internal defects will be detected depending on the selected mode and on the selected angle of incidence for a given strip thickness.

The symmetrical mode (s) is usually preferred because it is faster due to its higher group velocity.

Six modes of Lamb waves are used in the EUROPA system, i.e , $S_0$, $S_1$, $S_2$ and $A_0$, $A_1$, $A_2$. Depending on where the pointing vector (which is indicating the energy flow or the power flux density) will reach a maximum, surface or internal defects will be identified.

Electromagnetic acoustic transducers (EMATs) are an excellent method of producing Lamb waves since they require no fluid couplant. In addition, the wavelength of Lamb waves produced by EMATs is determined by the separation of adjacent conductors and the frequency can be easily changed by a software command. EMATs have been used for all types of inspections involving thin wall components of various shapes and defects in welds. EMAT Lamb waves are particularly suited to high speed automated inspections because there are no couplant limitations.

The prior art does not disclose or suggest how to select a Lamb wave mode that would be used for on-line detection of pencil pipe defects in strip steel before the strip is rolled to its final thickness. The pencil pipe inclusions are thought to result from extraneous non-metallic material trapped in the ingot that finally gets rolled into a thin inclusion or delamination. The defect normally occurs close to the edge of the strip (within 25" of the edge).

Thus there still is a need for an on line system for detecting of pencil pipe defects in strip steel using EMAT and optimized Lamb waves.

SUMMARY OF THE INVENTION

The present invention is directed to solving the problems associated with prior art strip steel inspection systems as well as others by providing a new and improved system for non-destructive inspection of surface defects and internal pencil pipe defects in strip steel through the use of EMAT and Lamb waves. The present invention has among its principal features the ability to position an EMAT (electromagnetic acoustic transducer) assembly along the surface of the sheet metal to scan the entire strip surface, receive, record, monitor and analyze the electrical signal produced in the receiver coil by the reflected surface wave to indicate the presence of a defect such as a crack, scratch, or sliver in the strip surface, and pencil pipe defects in the sub-surface, and communicate electronically with the strip steel process apparatus.

The present invention replaces the need for conventional eddy current and ultrasonic inspection systems by combining the ability to detect both surface defects and subsurface pencil pipe flaws into one rapid inspection operation. The advantages include significantly improved performance, reliability and efficiency of the sheet metal process and elimination of the need for an inspection operator.

The present invention also referred to as Temate® 4000 system provides volumetric inspection of strip steel for detection of internal and surface defects using EMATs. The Temate® 4000 system provides the following features:

1. Continuous operation in commercial, heavy industrial steel coil production mills, including pickling and final finishing lines.
2. Inspection of a full range of pickled hot rolled steel strip grades including regular, low, and ultra low carbon, and high strength low alloy.
3. Inspection of material gauge from about 0.050" to 0.200" in thickness.
4. Inspection of material from about 30 to 80 inches in width.
5. Inspection of 100% of the steel strip in all three dimensions: down-web, cross-web (except about 1.5" from each edge assumed to be trimmed later), and through-thickness.
6. Operation on strip moving at line speeds up to about 1,200 feet per minute, accelerating up to about 250fpm/sec, and decelerating up to about 275 fpm/sec.

The various features of novelty which characterize the present invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

DESCRIPTION OF THE PREFERRED EMBODIMENT

The present invention permits automated inspection of sheet metal coils for external defects and pencil pipe internal defects prior to the sheet metal being rolled or formed. Frequently, a long flat sheet of metal will be produced and wound into a coil after passing through a preliminary rolling process.

Figure 1:
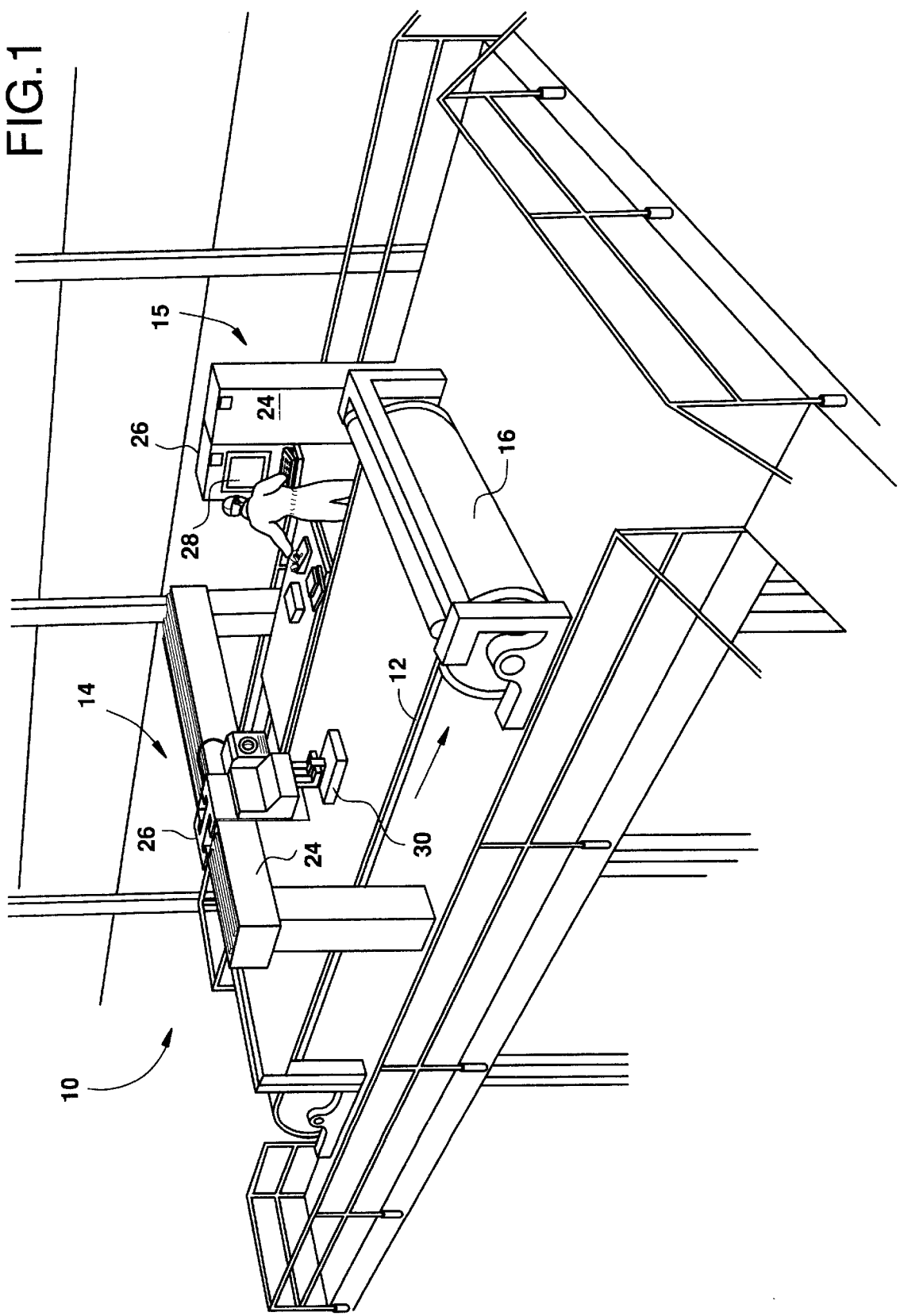
FIG. 1 is a perspective view of sheet metal station showing the inspection system with the EMATs mounted to scan the strip and the remote control and data acquisition system proximate to the sheet metal station.

This is where the inspection of the present invention is performed as best seen in FIG. 1. After this inspection, the coil may be transported to the first shearing apparatus located at another section of the factory and the end of that coil will be joined at the welding apparatus to the trailing end of another earlier transported coil which, for the most part, has already passed through a number of processing and treatment stations downstream of the welding apparatus.

The quality and integrity of steel rolls are key factors in the productivity of steel production facilities and the quality of the finished product.

Sheet metal is subject to external defects such as cracks, scratches, and slivers which may be seen by visible inspection. However, pencil pipe internal defects are unlikely to be seen with visual techniques. Reliable detection of both external and pencil pipe defects with the automated inspection system of the present invention provides the assurance that these defective strip conditions are identified prior to forming the final sheet metal coil for use and service.

Figure 2:
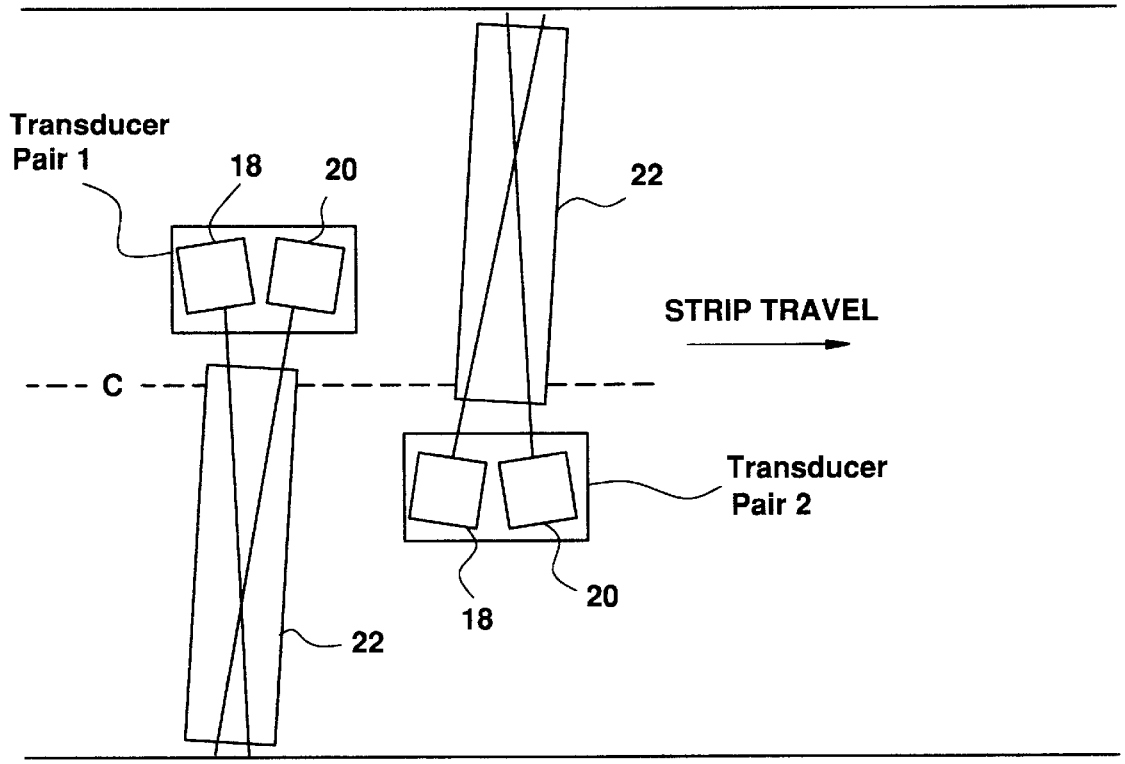
FIG. 2 is an expanded view of the sheet metal showing the mounting of the EMAT inspection system mounted to scan the strip.

FIGS. 1 and 2 show a sheet metal strip station (10) having sheet metal (12) with an EMAT defect inspection assembly (14) mounted to scan the strip (12). The assembly (14) is controlled by a data acquisition and control assembly (15) located in the area of the mill roll station (10). The assembly (14) has two transducer pairs 1 and 2with each having a transmitter coil (18) which produces an ultrasonic Lamb wave which travels into the metal as it is being processed. The wave is reflected and passes back to the EMAT receiver coil (20) as a reflected wave. Each transducer pair 1 and 2 has a respective coverage zone (22) as shown in FIG. 2.

The assembly (15) has a computer control unit (24) which is in electrical communication with the mill processing (16) apparatus and a data acquisition unit (26). A first cable (not shown) provides the electrical connection between the computer control unit (24) and the process apparatus (16). A second cable (not shown) electrically connects the computer control unit (24) to the data acquisition unit (26).

The EMAT sensor assembly (14) includes a first and second electromagnetic acoustic transducer positioned therein and attached to means for moving the assembly which rapidly scans the sheet metal (12) immediately prior to being processed. It provides nearly 100% inspection of both top and bottom surface and internal from its central location on the surface of the strip. Instantaneously, upon completion of an entire steel coil, a signal is presented to the operator and a detailed defect map is displayed at the console (28). The defect map indicates the individual defects, size, severity and location along the strip length and width. An inspection summary contains a running tally of the number and severity of defects.

Immediate disposition of the steel strip quality is thus provided to the operator as an easy to read defect map and inspection summary. Color display is used to readily indicate the size and severity of defects revealed during inspection. The results of each inspection are catalogued and stored within the system (15) and are uniquely traceable to each steel coil. This data can be recalled and displayed for post inspection evaluation.

The sensor positioning system (14) is mounted to straddle the moving steel coil (12) and includes a gantry frame (24), movable carriage (26), and two compliancy fixture assemblies used to support the EMAT probes (not shown).

The integrated control cabinets of the system (15) are mounted adjacent to each other and to the sensor positioning system (14) and environmentally houses the system which together is known as the TEMATE® 4000 system. The control computer, monitor, keyboard, and EMAT electronics operate in accordance with the schematics shown and described in U.S. Pat. No. 5,439,157 which is hereby incorporated by reference. Operating personnel can utilize the integrated control cabinet for system testing, parameter set-up, programming, and real-time and post-inspection data evaluation.

The carriage (26) is automatically positioned between inspection and maintenance positions using a pneumatic cylinder.

Probe compliancy fixture assemblies are connected to the carriage(26) using pneumatic linear actuators for vertically extending and retracting the EMAT probes onto the surface (12). The probe compliancy fixture provides compliancy of the EMAT probes with the strip surface (12). The probe compliancy fixture incorporates high durometer urethane rollers (30) designed for high speed steel strip applications to maintain precise probe to strip spacing and to minimize the possibility of marking the strip. Rollers (30) have a life of four (4) months under normal operating conditions. The rollers (30) are the only items in contact with the steel strip (12). The probe compliancy fixture pneumatics provide the ability to rapidly retract the probe fixture to avoid damage from untrimmed welds and to facilitate coil assembly changes. The system initiates retraction and redeployment of the fixtures for oncoming welds based on input from the line control system. Retraction cycle is less than one (1) second. Input to the data acquisition system (15) during retraction is provided to accurately indicate non-inspected areas around untrimmed welds.

The probe compliancy fixture assemblies incorporate quick disconnect mechanical and electrical connections for rapid removal and replacement of EMAT probes. The sensor positioning system incorporates electrically isolated connections to minimize degrading ground loops and electrical noise. The sensor transport automatically extends the appropriate set of probes onto the strip surface.

An industrial enclosure (26) is provided adjacent to the sensor positioning system (14) to house the host computer, EMAT electronics, and personnel interface monitor and keyboard.

A separate parallel operator interface monitor and keyboard (28) is provided and may be located up to 200 feet from the control cabinet.

The system (14) includes two (2) pulsed DC magnets and EMAT coil assemblies. Each coil assembly includes two or more EMAT coils, each capable of generating ultrasonic waves sensitive to a particular range of strip (12) thickness. 100% of the strip is inspected in all three dimensions: down-web (rolling direction), cross-web (transverse direction), and through-thickness. The fixture supports two EMAT probes for inspection of each half of the strip width as shown in FIG. 2. The opposing EMAT probes are positioned to overlap the center of the strip (c) to ensure 100% coverage and eliminate dead zones under the sensors. Each EMAT coil inspects a gauge range of +/−10% of nominal gauge for that coil. The use of multiple EMAT coils under each magnet allows uninterrupted inspection of multiple gauge ranges without change-out of sensors. Each EMAT coil is protected from incidental contact with the steel strip by a protective surface. The protective surface does not contact the steel strip surface. The EMAT coil is rigidly attached to the magnet.

The system of the present invention utilizes EMAT ultrasonic Lamb wave modes to detect and differentiate surface and internal defects. One wave is tuned for sensitivity to internal delaminations, whereas, the other is tuned for sensitivity to surface defects only. The wave tuned to internal defects operates at a frequency ranging from about 400 $KH_z$ to 2 $MH_z$, with a preferred frequency dependent on sheet metal gauge while the wave tuned to the surface defects operates at frequency ranging from about 600 $KH_z$ to 3.4 $MH_2$ with preferred frequency dependent on sheet metal gauge. The system automatically compares the signal reflections from these two ultrasonic waves to discriminate between surface and internal defects based upon calibrated standards. The invention provides detection of internal defects with minimum size of about 0.5000" length (in the rolling direction) by about 0.0100" width (in the transverse direction) by about 0.0004" thickness (in the direction of strip thickness). Resolution is about 0.50"or better along the cross-web (transverse) dimension. Maximum resolution in the down-web (rolling direction) is dependent upon strip speed. The system provides sampling resolution down to about 0.50" at a line speed of 1000 feet per minute. Processed data from all pairs of EMAT sensors is automatically combined to provide a single signal corresponding to the full inspected width of the coil. The signal displays the representative location of the defect according to the operator or drive side of the strip. EMAT pre-amplifier electronics are located directly above the fixture assemblies on the carriage to maximize signal integrity.

Edge reflection data received from the EMAT sensors is used to automatically compensate for up to 6" shift of the strip centerline. Signals displayed reflect location with respect to the strip centerline.

EMAT signal amplitude may be optionally displayed relative to the amplitude of the edge reflection signal.

Figure 3:
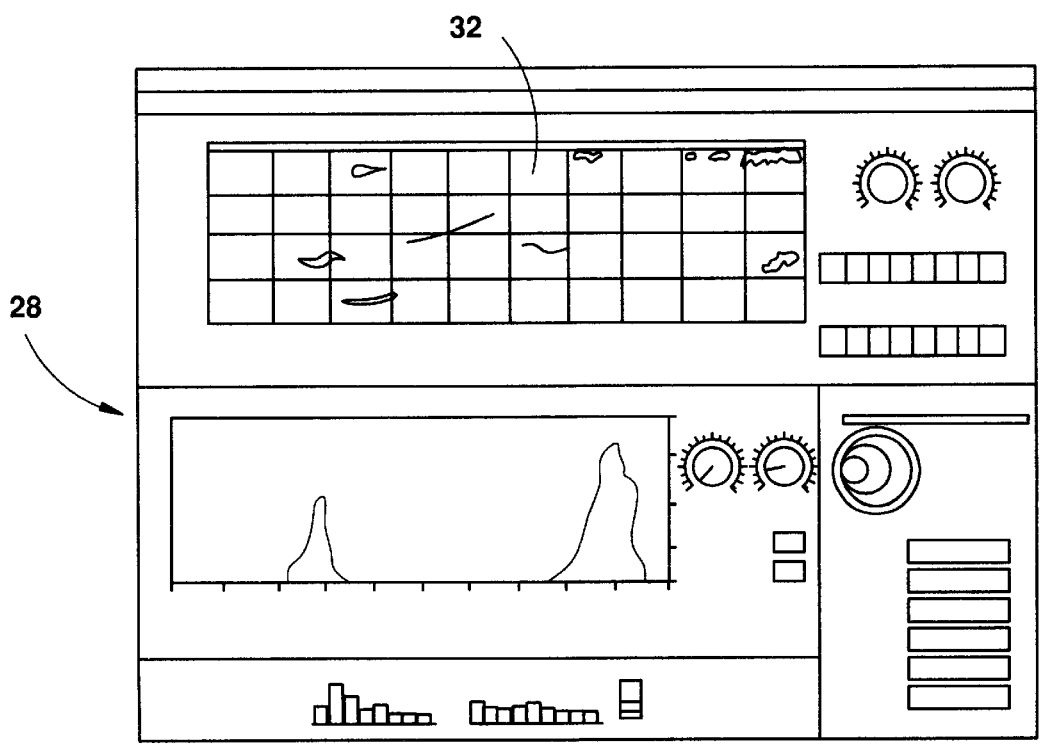
FIG. 3 is an expanded front view of the display screen of the remote operator display.

As best seen in FIG. 3, the inspection system (14) provides continuous display of a real-time defect map and defect summary of the coil being inspected on a CRT operator interface terminal (28).

The real-time defect map (32) is a scrolling display showing individual defects as they are detected during the inspection. The graphical location of defects are representative of its location along two axes (down-web vs. cross-web). The cross-web location is displayed relative to the centerline of the strip. Color is used to indicate the strength of the signal corresponding to the defect, and its classification as either surface flaws, or internal flaws. The size and color of the displayed defect provides an indication of the size and severity of the defect.

The real-time defect summary contains a running tally of the number of internal and surface defects detected according to defect severity for the coil being inspected. The summary also displays general operating information, including; coil number, product type, customer, strip width, time and date.

The Temate® 4000 system produces a hard copy report of the defect map, automatically at the end of each coil or on demand, that corresponds to the real-time defect map as presented on the operator interface. The Temate® 4000 system also produces a hard copy inspection summary report, automatically at the end of each coil or upon demand, of the results of the inspection for each coil inspected. The inspection summary report for each coil inspection shows the number of defects and classification found in each of 8 "lanes" across the strip and in each increment of from five (5) to one hundred (100) feet down the length of the strip.

The total number of flaws, by severity and classification found in each "lane" and along each length increment of the entire coil is provided. The summary report also includes general operating information including; coil number, customer, product type, strip width and time and date.

The system (15) catalogs and stores images of signals corresponding to all flaw indications to removable storage media. Images of signals corresponding to selected defects can be recalled and displayed from a removable storage media in a selected drive as with normal computer systems.

While a specific embodiment of the invention has been shown and described in detail to illustrate the application of the principles of the invention, it will be understood that the invention may be embodied otherwise without departing from such principles.

What is claimed is:

1. An automated inspection system for non-destructively examining strip sheet metal moving in a strip travel direction for pencil pipe defects prior to rolling, or forming, the sheet metal strip having a width transverse to the travel directions, the inspection system comprising:

a first transmitting electromagnetic acoustic transducer mounted for movement over a sheet metal strip moving in the strip travel direction, said first transmitting electromagnetic acoustic transducer propagating an ultrasonic Lamb wave into a first coverage zone extending partly across the width of the sheet metal strip;

a first receiving electromagnetic acoustic transducer mounted for movement over the sheet metal strip, said first receiving electromagnetic transducer receiving a reflected ultrasonic Lamb wave from said first coverage zone;

a second transmitting electromagnetic acoustic transducer mounted for movement over the sheet metal strip, said second transmitting electromagnetic acoustic transducer propagating an ultrasonic Lamb wave into a second coverage zone extending partially across the width of the sheet metal strip, a second receiving electromagnetic acoustic transducer mounted for movement over the sheet metal strip, said second receiving electromagnetic transducer receiving a reflected ultrasonic Lamb wave from said second coverage zone;

computer control means connected to and in communication with said first and second electromagnetic acoustic acoustic transducers for coordinating the inspection of the sheet metal strip for said pencil pipe defects; and data acquisition means connected to and in communication with all of said computer control means for receiving, storing, displaying and analyzing information provided from said computer control means and for transmitting information thereto, said data acquisition means detecting any defects in the sheet metal strip which has moved in the travel direction based on changes in the ultrasonic Lamb wave.

2. A system according to claim 1, wherein each receiving electromagnetic acoustic transducer includes an electrostatic shield for protecting each receiving electromagnetic acoustic transducer from electromagnetic interference and radio frequency interference.

3. A system according to claim 1, including a first wave generator for each transmitting transducer for producing a Lamb wavelength for detecting surface cracks in a sheet of metal along with pencil pipe internal defects.

4. A system according to claim 1, wherein said first transmitting electromagnetic acoustic transducer, said first receiving electromagnetic acoustic transducer, said second transmitting electromagnetic acoustic transducer, and said second receiving electromagnetic acoustic transducer are positioned in at least one assembly attached to means for moving the at least one assembly for scanning the sheet metal strip for surface breaking defects such as scratches or gouges.

5. A system according to claim 4, wherein said first and second coverage zones overlap and cover the full width of the sheet metal strip.

6. A system according to claim 5, including a central line of the sheet metal strip width extending in the travel direction, the first coverage zone being mostly on one side of the central line and the second coverage being mostly on the opposite side of the central line.

7. A method of inspecting sheet metal for surface and sub-surface defects prior to rolling or forming, comprising the steps of:

moving the sheet metal in a travel direction, the sheet metal having a width;

propagating an ultrasonic Lamb wave into a first coverage zone extending partly across the width of the sheet metal with a first transmitting electromagnetic acoustic transducer;

receiving a reflected ultrasonic Lamb wave from the first coverage zone of the sheet metal with a first receiving electromagnetic acoustic transducer;

propagating an ultrasonic Lamb wave into a second coverage zone extending partly across the width of the sheet metal with a second transmitting electromagnetic acoustic transducer;

receiving a reflected ultrasonic Lamb wave from the second coverage zone of the sheet metal with a second receiving electromagnetic acoustic transducer;

generating transmitted signals from said first and second transmitting electromagnetic acoustic transducers and received signals from said first and second receiving electromagnetic acoustic transducers with data acquisition means connected to both of said transmitting electromagnetic acoustic transducers and both of said receiving electromagnetic acoustic transducers;

determining from the transmitted and received signals any internal pencil pipe defects in the sheet metal with computer control means; and displaying information regarding any defects in the sheet metal.

8. A method according to claim 7, further comprising the step of scanning the entire sheet metal as the sheet metal moves in the travel direction.

9. A method according to claim 8, wherein the first and second coverage zones cover the entire width of the sheet metal.

10. A method according to claim 9, wherein the sheet metal includes a central line parallel to the travel direction, the first coverage zone being mostly on one side of the central line and the second coverage zone being mostly on the opposite side of the central line.

* * * * *